US009244179B2

(12) United States Patent
Lau et al.

(10) Patent No.: US 9,244,179 B2
(45) Date of Patent: Jan. 26, 2016

(54) TIME-BASED DIGITIZER FOR PET PHOTODETECTOR

(71) Applicant: The Board of Trustees of the Leland Stanford Junior University, Palo Alto, CA (US)

(72) Inventors: Frances W. Y. Lau, Sunnyvale, CA (US); Craig Steven Levin, Palo Alto, CA (US); Mark A. Horowitz, San Mateo, CA (US); Hwang Ho Choi, Stanford, CA (US); Jaeha Kim, Seoul (KR)

(73) Assignee: The Board of Trustees of the Leland Stanford Junior University, Palo Alto, CA (US)

(*) Notice: Subject to any disclaimer, the term of this patent is extended or adjusted under 35 U.S.C. 154(b) by 0 days.

(21) Appl. No.: 14/360,289

(22) PCT Filed: Dec. 4, 2012

(86) PCT No.: PCT/US2012/067800
§ 371 (c)(1),
(2) Date: May 22, 2014

(87) PCT Pub. No.: WO2013/085923
PCT Pub. Date: Jun. 13, 2013

(65) Prior Publication Data
US 2015/0001404 A1 Jan. 1, 2015

Related U.S. Application Data (60) Provisional application No. 61/567,322, filed on Dec. 6, 2011.

(51) Int. Cl.
*G01T 1/166* (2006.01)
*G01T 1/29* (2006.01)
(Continued)

(52) U.S. Cl.
CPC ............ *G01T 1/208* (2013.01); *E02D 29/1427* (2013.01); *G01T 1/1647* (2013.01);
(Continued)

(58) Field of Classification Search
CPC ......... G01T 1/20; G01T 1/202; G01T 1/2023; G01T 1/2002; G01T 1/2985; G01T 1/1642; G01T 1/1615; G01T 1/1611; G21K 4/00
USPC ........................................ 250/361 R–363.04
See application file for complete search history.

(56) References Cited

U.S. PATENT DOCUMENTS 4,057,796 A * 11/1977 Hoogendoorn et al. ...... 341/157
5,130,667 A    7/1992 Chang et al.
(Continued)

OTHER PUBLICATIONS

Lau et al., "A New IC with Level-Crossing ADC Readout Architecture for PET Detector Signals," IEEE Nuclear Science Symposium and Medical Imaging Conference Record (NSS/MIC), 2012, pp. 2486-2488.
(Continued)

*Primary Examiner* — David Porta
*Assistant Examiner* — Mamadou Faye
(74) *Attorney, Agent, or Firm* — Beyer Law Group LLP (57) ABSTRACT

An integrated circuit in a PET imaging system with a plurality of photo detectors is provided. A plurality of differential transimpedance amplifiers with differential inputs and differential outputs is provided, wherein differential inputs for each differential transimpedance amplifier of the plurality of differential transimpedance amplifiers are electrically connected to a photodetector. A plurality of level crossing analog-to-digital converters is provided wherein differential inputs for each level crossing analog-to-digital converter of the plurality of level crossing analog-to-digital converters are electrically connected to differential outputs of a differential transimpedance amplifier, wherein each level crossing analog-to-digital converter of the plurality of level crossing analog-to-digital converters, comprises a plurality of differential comparators with differential inputs and differential threshold inputs, wherein the differential inputs are electrically connected to the output of the differential outputs of the differential transimpedance amplifier electrically connected to the level crossing analog-to-digital converter and a clock.

16 Claims, 7 Drawing Sheets

(51) Int. Cl.
*G01T 1/208* (2006.01)
*H03M 1/10* (2006.01)
*H03F 3/08* (2006.01)
*H03M 1/20* (2006.01)
*E02D 29/14* (2006.01)
*G01T 1/164* (2006.01)
*G01T 1/20* (2006.01)
*G01T 1/202* (2006.01)
*A61B 6/03* (2006.01)
*A61B 6/00* (2006.01)

(52) U.S. Cl.
CPC .............. *G01T 1/202* (2013.01); *G01T 1/2006* (2013.01); *G01T 1/2985* (2013.01); *H03F 3/08* (2013.01); *H03M 1/1019* (2013.01); *H03M 1/204* (2013.01); *A61B 6/037* (2013.01); *A61B 6/4208* (2013.01)

(56) References Cited

U.S. PATENT DOCUMENTS

| | | | |
|---|---|---|---|
| 6,552,605 B1 | 4/2003 | Yoon | |
| 7,212,144 B1* | 5/2007 | Sutardja | 341/159 |
| 7,466,258 B1 | 12/2008 | Akopyan et al. | |
| 7,577,226 B2* | 8/2009 | Sou | 375/376 |
| 7,825,735 B1* | 11/2010 | Wessendorf | 330/308 |
| 2003/0048213 A1* | 3/2003 | Sushihara et al. | 341/159 |
| 2009/0224158 A1 | 9/2009 | Haselman | |
| 2010/0078569 A1 | 4/2010 | Jarron et al. | |
| 2010/0123520 A1* | 5/2010 | Shifrin | 330/254 |
| 2010/0142610 A1 | 6/2010 | Stojanovic et al. | |
| 2010/0210950 A1 | 8/2010 | Dunbar | |
| 2010/0294944 A1* | 11/2010 | Furumiya et al. | 250/370.1 |

OTHER PUBLICATIONS

International Search Report dated Apr. 1, 2013 from International Patent Application No. PCT/US2012/067800.

Written Opinion dated Apr. 1, 2013 from International Patent Application No. PCT/US2012/067800.

Xie et al., "A New Approach for Pulse Processing in Positron Emission Tomography," IEEE Transactions on Nuclear Science, vol. 52, No. 4, Aug. 2005, 8 pages.

Wang et al., "Initial Implementation of All-Digital PET DAQ System," Nuclear Science Symposium Conference Record (NSS/MIC), 2010 IEEE, Conference date Oct. 30, 2010-Nov. 6, 2010, pp. 2500-2503.

Powolny et al., "Time-Based Readout of a Silicon Photomultiplier (SiPM) for Time of Flight Positron Emission Tomography (TOF-PET)," IEEE Transactions on Nuclear Science, vol. 58, No. 3, Jun. 2011, pp. 597-604.

Kim et al., "A multi-threshold sampling method for TOF-PET signal processing," Nuclear Instruments and Methods in Physics Research A, 602 (2009) pp. 618-621.

* cited by examiner

FIG. 3 differential transimpedance amplifier
(differential TIA)

FIG. 4A regulated cascode transimpedance amplfiier half-circuit

TIME-BASED DIGITIZER FOR PET PHOTODETECTOR

CROSS REFERENCE TO RELATED APPLICATIONS

This application claims priority under 35 U.S.C. §119 from U.S. Provisional Patent Application No. 61/567,322, filed Dec. 6, 2011, entitled ADJUSTABLE AMPLIFIER AND TIME-BASED DIGITIZER WITH FAST TIMING FOR SIPM-AND ADP-BASED PET PHOTODETECTORS, which is incorporated herein by reference for all purposes.

FIELD OF THE INVENTION

A field of the invention is imaging. Example applications of the invention include, but are not limited to imaging using a photodetector. A more specific application of the invention provides a readout for photodetectors in a positron emission tomography system.

BACKGROUND OF THE INVENTION

Positron emission tomography (PET) is a diagnostic imaging modality that is used to non-invasively measure the biodistribution of a radioactive tracer. In positron emission tomography, a positron emitting bare radioactive isotope or an isotope that has been attached to a chemical molecule, is injected into a patient or animal. A positron is emitted by the radioactive isotope and annihilates with an electron producing two photons in opposite directions. Each of the photons has approximately 511 keV of energy, corresponding to the mass of the positron and electron. These two annihilation photons escape the patient and interact in a scanner that is positioned around the patient.

A scanner is made of arrays of high energy photon detectors that convert interactions in the detector into electrical signals that are processed on a computer. An example of a high energy photon detector is a scintillation crystal that is connected to an optical photodetector such as a photomultiplier tube. The 511 keV annihilation photon can interact in the high-Z dense scintillation crystal, which in turn emits blue photons that bounce inside of the scintillation crystal. The blue optical photons then hit a photodetector which converts the light into an electrical signal. The electrical signal is then processed by analog and digital electronic circuits and is recorded as an event. The electronics process the signal and records the time, location of the crystal that was hit, and the energy of high energy annihilation photon to storage. In positron emission tomography, the two photons are paired to produce a line-of-response (LOR) of the interaction. These LORs are processed by image reconstruction algorithms to produce 3-D images of the distribution of the radiotracer. High energy photon detector elements are placed around the object to be imaged covering a certain solid angle or angular coverage. The solid angle, or angular coverage around the object to be imaged, plus the efficiency of stopping and detecting the annihilations photons determines the sensitivity of the depth-of-interaction scanner. A scanner with a higher sensitivity will potentially have a better image quality or a shorter scan time than a scanner with a lower sensitivity. The cost of a scanner is directly related to the number of detection elements in the system. The scanning geometry is designed to optimize the sensitivity as a function of cost, size, and disposition of the object being imaged.

SUMMARY OF THE INVENTION

Embodiments of the invention provide, an integrated circuit in a PET imaging system with a plurality of photodetectors. A plurality of differential transimpedance amplifiers with differential inputs and differential outputs is provided, wherein differential inputs for each differential transimpedance amplifier of the plurality of differential transimpedance amplifiers are electrically connected to a photodetector of the plurality of photodetectors. A plurality of level crossing analog-to-digital converters is provided wherein differential inputs for each level crossing analog-to-digital converter of the plurality of level crossing analog-to-digital converters are electrically connected to differential outputs of a differential transimpedance amplifier of the plurality of differential transimpedance amplifiers, wherein each level crossing analog-to-digital converter of the plurality of level crossing analog-to-digital converters, comprises a plurality of differential comparators with differential inputs and differential threshold inputs, wherein the differential inputs are electrically connected to the output of the differential outputs of the differential transimpedance amplifier of the plurality of differential transimpedance amplifiers electrically connected to the level crossing analog-to-digital converter and a clock for providing a time stamp.

In another manifestation of the invention a PET imaging system is provided. A plurality of scintillation crystals is provided. A plurality of photodetectors is provided, wherein each photodetector of the plurality of photodetectors is positioned to receive photons from a scintillation crystal of the plurality of scintillation crystals. An integrated circuit is provided, comprising a plurality of differential transimpedance amplifiers with differential inputs and differential outputs, wherein differential inputs for each differential transimpedance amplifier of the plurality of differential transimpedance amplifiers are electrically connected to a photodetector of the plurality of photodetectors and a plurality of level crossing analog-to-digital converters wherein differential inputs for each level crossing analog-to-digital converter of the plurality of level crossing analog-to-digital converters is electrically connected to differential outputs of a differential transimpedance amplifier of the plurality of differential transimpedance amplifiers. Each level crossing analog-to-digital converter of the plurality of level crossing analog-to-digital converters comprises a plurality of differential comparators with differential inputs and differential threshold inputs, wherein the differential inputs are electrically connected to the output of the differential outputs of the differential transimpedance amplifier of the plurality of differential transimpedance amplifiers electrically connected to the level crossing analog-to-digital converter and a clock The invention and objects and features thereof will be more readily apparent from the following detailed description and appended claims when taken in conjunction with the drawings.

DETAILED DESCRIPTION

Figure 1A:
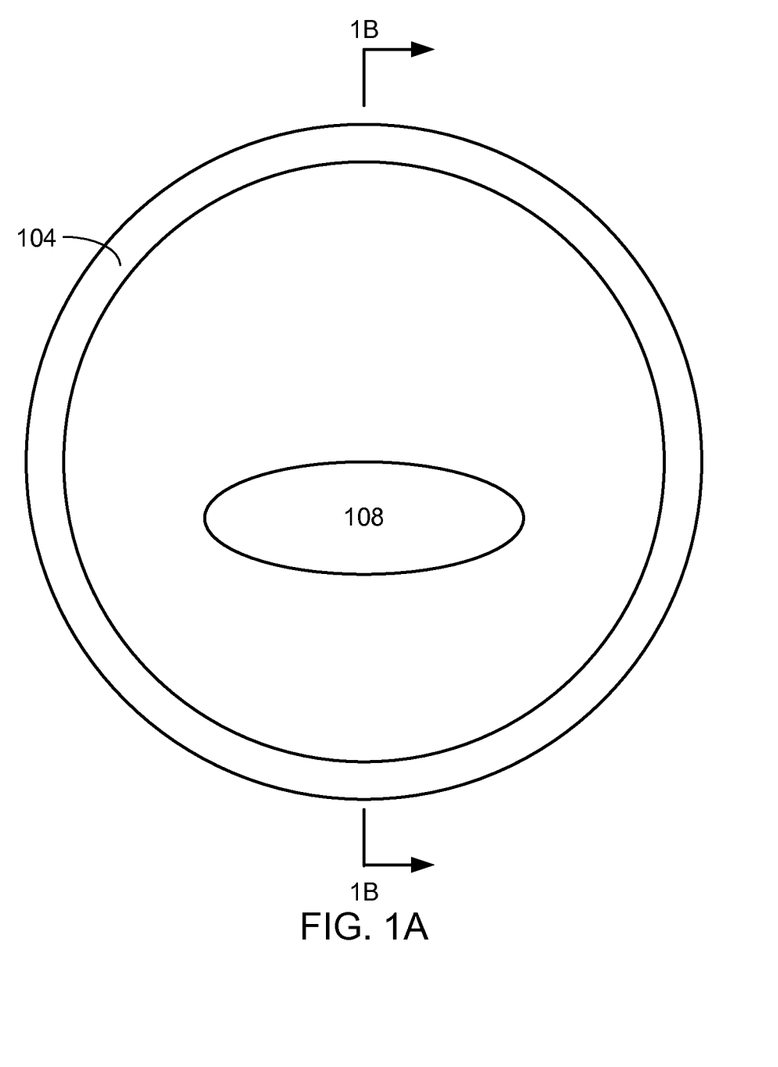
FIG. 1A is a cross sectional view of a PET scanner with an object.
Figure 1B:
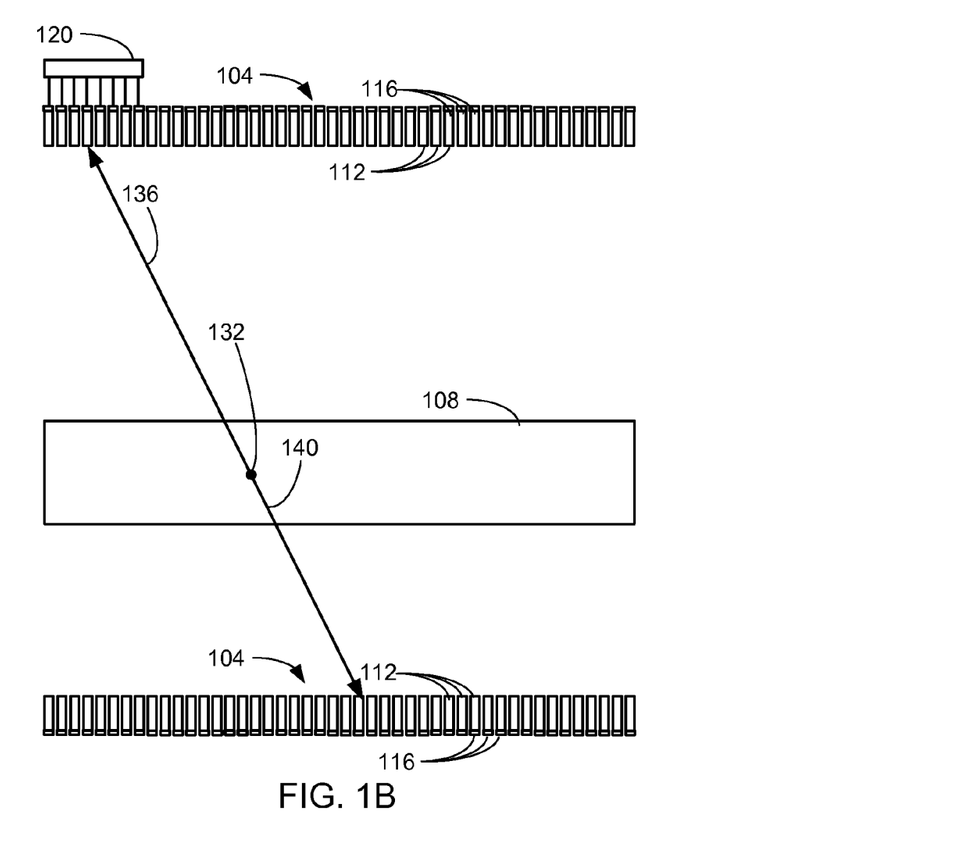
FIG. 1B is a cross sectional view of the PET scanner along cut line 1B that shows that the PET scanner is made of a plurality of individual scintillation crystals.

FIG. 1A is a cross sectional view of a PET scanner 104 with an object 108 that is used in an embodiment of the invention. FIG. 1B is a cross sectional view of the PET scanner 104 along cut line 1B that shows that the PET scanner 104 is made of a plurality of individual scintillation crystals 112. Each scintillation crystal 112 optically coupled to at least one photodetector 116, so that that photodetector 116 receives photons from the scintillation crystal 112. The photodetector 116 may be, for example, a position sensitive avalanche photodiode (PSAPD), a silicon photomultipliers (SiPM), or a photomultiplier tube. Preferably, the photodetector 116 is a SiPM. Each photodetector 116 is connected to a readout device 120. Only one of the readout devices is shown. In this example, the readout device 120 that is shown is connected to eight photodetectors 116.

Figure 2:
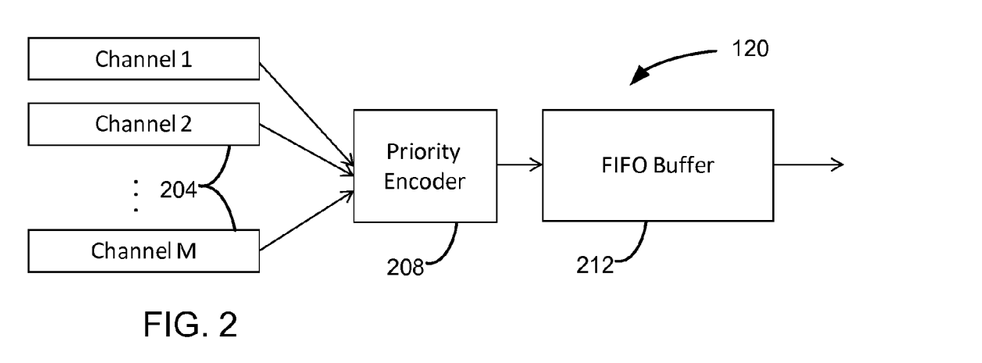
FIG. 2 is a circuit block diagram of a readout device.

FIG. 2 is a circuit block diagram of the readout device 120. The readout device 120 is able to handle M channels, with each channel providing a readout for a scintillation crystal 112, FIG. 1B. Data from the channels 204 is provided to a priority encoder 208, which provides input to a first in first out (FIFO) buffer 212.

Figure 3:
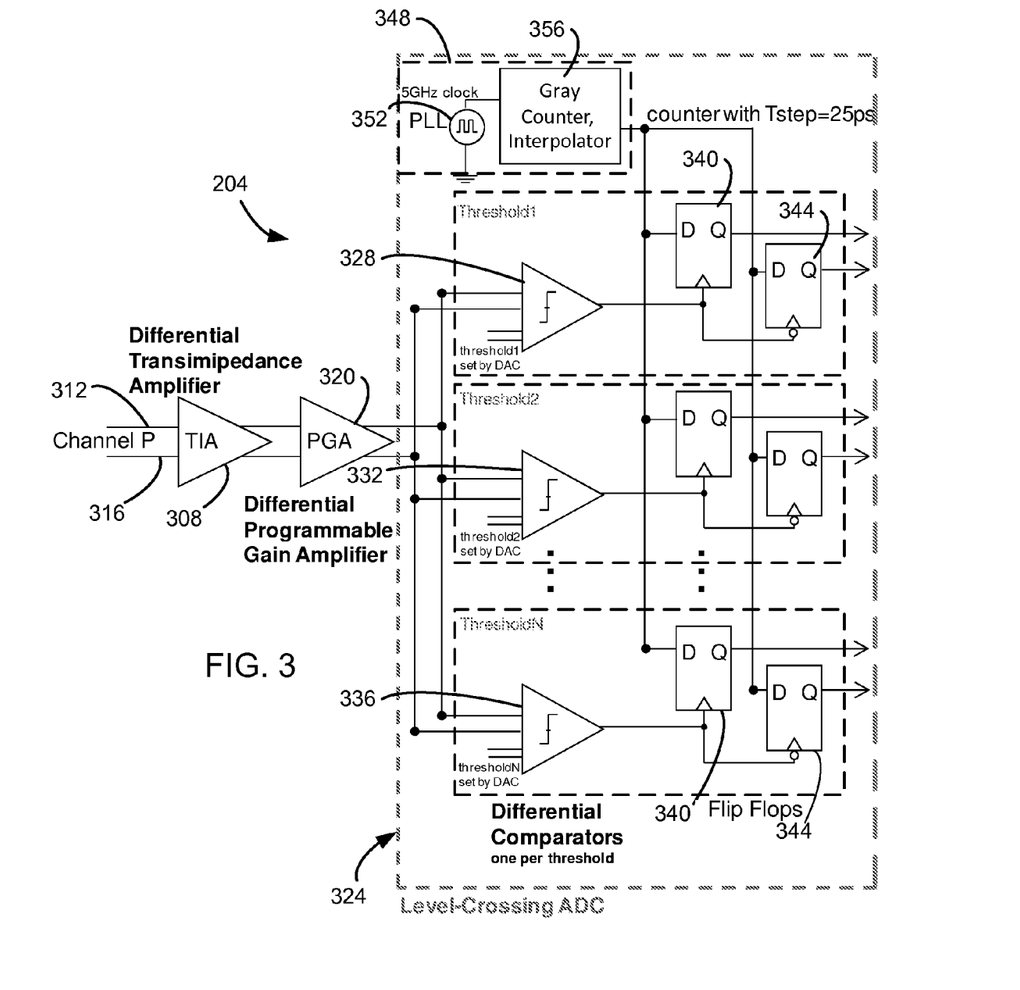
FIG. 3 is a schematic view of a circuit for a channel.
Figure 4A:
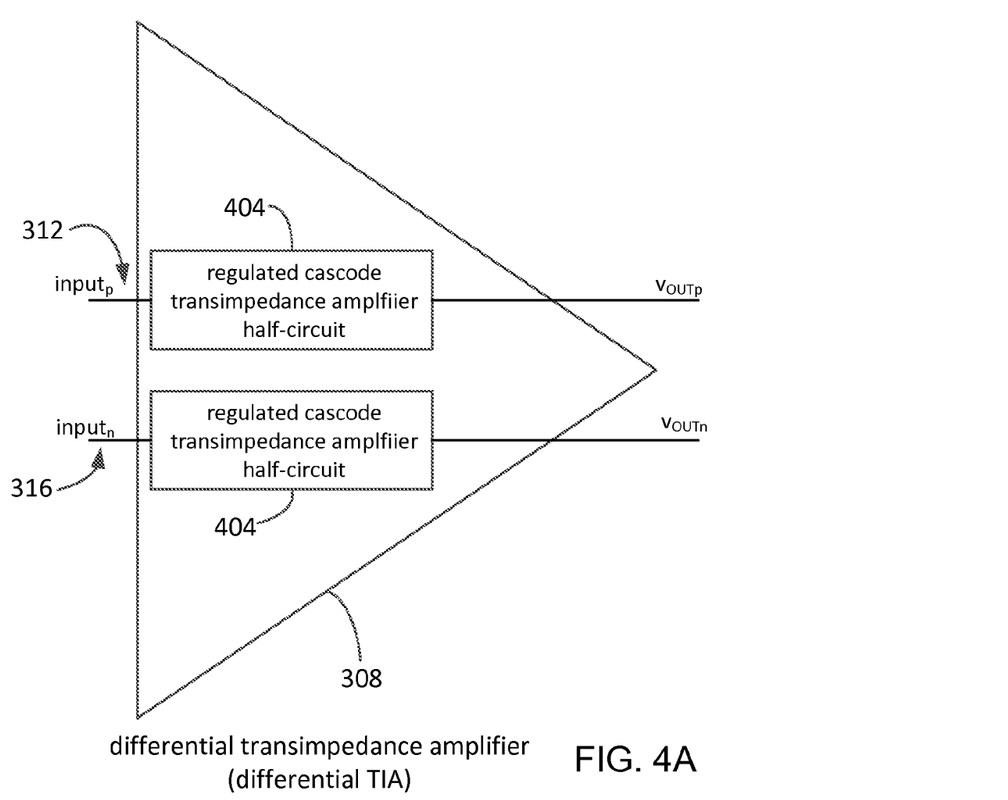
FIG. 4A is a schematic view of a differential transimpedance amplifier used in an embodiment of the invention.
Figure 4B:
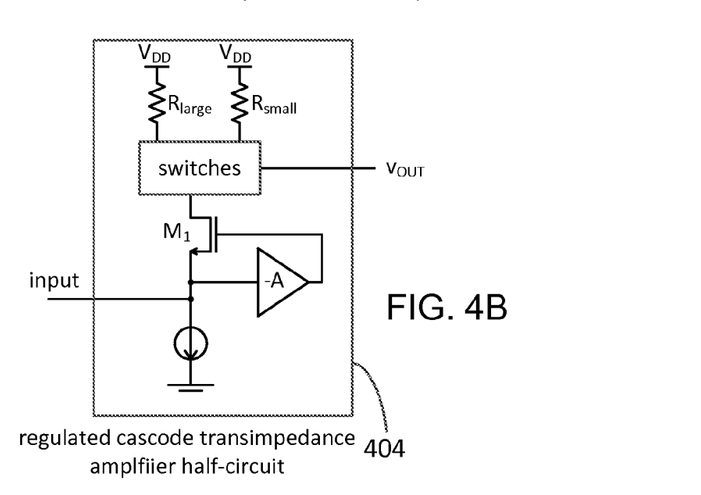
FIG. 4B is a schematic view of a regulated cascode transimpedance amplifier half circuit used in the differential transimpedance amplifier, shown in FIG. 4A.

FIG. 3 is a schematic view of a circuit for a channel 204. The circuit comprises a differential transimpedance amplifier (TIA) 308 that receives a first input 312 and a second input 316 from the photodetector 116. The first input 312 and second input 316 are compared to reduce noise. The differential TIA 308 converts an input current signal to an output voltage signal. FIG. 4A is a schematic view of a differential TIA 308 used in this embodiment of the invention. The differential TIA consists of two regulated cascode transimpedance amplifier half-circuits 404. FIG. 4B is a more detailed schematic view of the regulated cascode TIA half-circuit 404. The regulated cascode architecture allows the possibility of a low input impedance. The regulated cascode transimpedance amplifier half-circuit has two load resistors, $R_{large}$ and $R_{small}$. The user can choose one of the two load resistors using the switches to allow the gain and input impedance to be modified over a wide range. Choosing $R_{small}$ results in lower input impedance and lower gain, which is suitable for detectors which already have high gain such as SiPMs. Choosing $R_{large}$ results in higher input impedance and higher gain, which is suitable for detectors with low gain and higher dark noise such as avalanche photodiodes and PSAPDs.

The output voltage signal of the differential TIA 308 is provided as input to a differential programmable gain amplifier (PGA) 320. The differential TIA 308 provides two outputs, which the differential PGA 320 receives as two inputs to reduce noise. The output of the differential PGA 320 is provided to a level-crossing analog-to-digital converter (ADC) 324. The level-crossing ADC 324 comprises a plurality (N) of differential comparators. In this example, 256 differential comparators (N=256) are provided. A first differential comparator 328 receives first and second differential inputs from the differential PGA 320. The first differential comparator 328 also receives a first pair of threshold inputs. A second differential comparator 332 receives first and second differential inputs from the differential PGA 320. The second differential comparator 332 receives a second pair of threshold inputs. An Nth differential comparator 336 receives first and second differential inputs from the differential PGA 320. The Nth differential comparator 336 also receives a pair of Nth threshold inputs.

Figure 5:
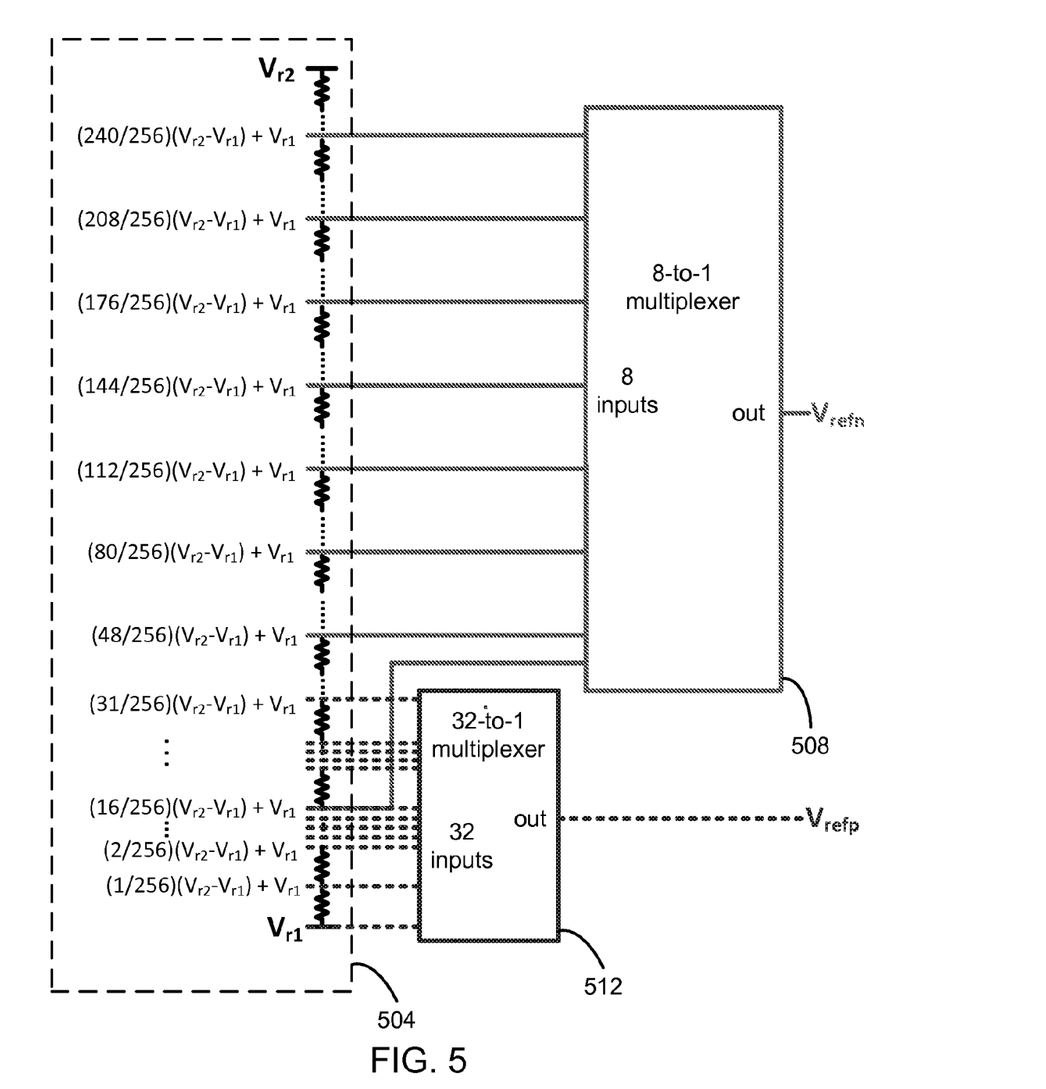
FIG. 5 is schematic view of a digital-to-analog converter used in an embodiment of the invention.

In order to tune the pairs of threshold inputs for the differential comparators 328, 332, 336 to an appropriate value, a digital-to-analog converter (DAC) is electrically connected to the pairs of threshold inputs via two n-to-1 multiplexers, which consists of a number of switches. FIG. 5 is schematic view of a DAC 504, an 8-to-1 multiplexer 508, and a 32-to-1 multiplexer 512. Positive nodes of the pairs of the threshold inputs for the differential comparators 328, 332, 336 are set by one of the 32 lowest available levels of the DAC 504 through the 32-to-1 multiplexer 512. The negative nodes of the pairs of threshold inputs for the differential comparators 328, 332, 336 are set by one of the 8 levels of the DAC 504 through the 8-to-1 multiplexer 508, where these 8 levels that are input into the multiplexer 508 are spaced out to span over the available levels of the DAC 504. In this example each of the 8 levels are spaced from each other with a spacing of 32 steps, where one step is equal to $(1/256)(V_{r2}-V_{r1})$. The spacing of the levels should be at most equal to 32 steps, that is, the number of steps spanned by the 32-to-1 multiplexer 512 plus one. The five lower bits set the value of the positive node of the pairs of threshold inputs, and the three higher bits set the value of the negative node of the pairs of threshold inputs. All of the combinations of the pairs of threshold inputs driven by the 8-to-1 multiplexer 508 and the 32-to-1 multiplexer provide 256 combinations or levels of differential thresholds for the differential comparators 328, 332, 336.

The output of each differential comparator 328, 332, 336 is provided to a first flip flop circuit 340 and a second flip flop circuit 344. Each first flip flop circuit 340 and a second flip flop circuit 344 is connected to a counter 348 and provides latched counter values to the priority encoder 208. In this embodiment, the counter 348 comprises a 5 GHz phase-locked loop 352 with a Gray Counter and Interpolator 356, which provides a 25 ps resolution.

Figure 6:
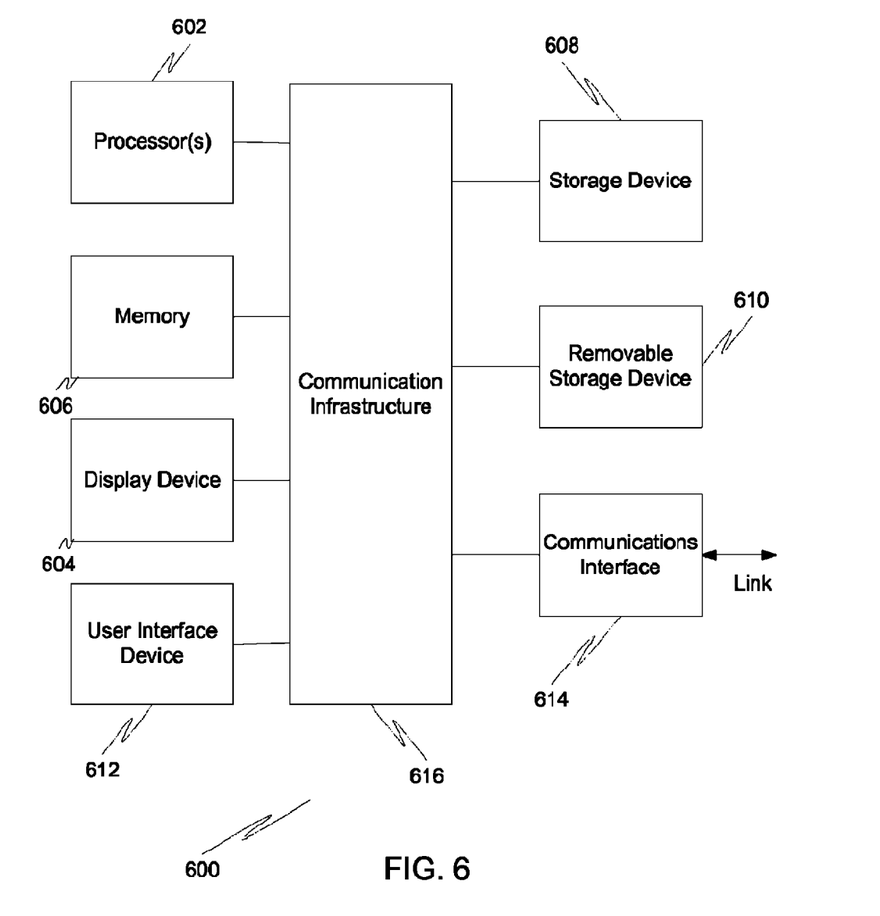
FIG. 6 is a high level block diagram showing a computer system.

Data from the channels 204 are passed to the priority encoder 208, which stores the data in the FIFO buffer 212, which provides the data to a computer system. FIG. 6 is a high level block diagram showing a computer system 600, to which the FIFO buffer 212 may be attached. The computer system may have many physical forms ranging from an integrated circuit, a printed circuit board, and a small handheld device up to a huge super computer. The computer system 600 includes one or more processors 602, and further can include an electronic display device 604 (for displaying graphics, text, and other data), a main memory 606 (e.g., random access memory (RAM)), storage device 608 (e.g., hard disk drive), removable storage device 610 (e.g., optical disk drive), user interface devices 612 (e.g., keyboards, touch screens, keypads, mice or other pointing devices, etc.), and a communication interface 614 (e.g., wireless network interface). The communication interface 614 allows software and data to be transferred between the computer system 600 and external devices via a link. The system may also include a communications infrastructure 616 (e.g., a communications bus, crossover bar, or network) to which the aforementioned devices/modules are connected.

Information transferred via communications interface 614 may be in the form of signals such as electronic, electromagnetic, optical, or other signals capable of being received by communications interface 614, via a communication link that carries signals and may be implemented using wire or cable, fiber optics, a phone line, a cellular phone link, a radio frequency link, and/or other communication channels. With such a communications interface, it is contemplated that the one or more processors 602 might receive information from a network, or might output information to the network in the course of performing the above-described method steps. Furthermore, method embodiments of the present invention may execute solely upon the processors or may execute over a network such as the Internet in conjunction with remote processors that shares a portion of the processing.

The term "non-transient computer readable medium" is used generally to refer to media such as main memory, secondary memory, removable storage, and storage devices, such as hard disks, flash memory, disk drive memory, CD-ROM and other forms of persistent memory and shall not be construed to cover transitory subject matter, such as carrier waves or signals. Examples of computer code include machine code, such as produced by a compiler, and files containing higher level code that are executed by a computer using an interpreter. Computer readable media may also be computer code transmitted by a computer data signal embodied in a carrier wave and representing a sequence of instructions that are executable by a processor.

Operation

In operation, in a PET scanner 104, a positron is emitted by the radioactive isotope and annihilates with an electron producing two photons in opposite directions. Each of the photons has approximately 511 keV of energy, corresponding to the mass of the positron and electron. FIG. 1B shows an annihilation location 132 and a path 136 for a first photon and a path 140 for a second photon. These two annihilation photons escape the patient and interact with the PET scanner 104 that is positioned around the object 108. Each high energy photon is absorbed in a scintillation crystal 112. The high energy photons have an energy that allows them to pass through some objects like photodetectors 116, and therefore are often not detected by photodetectors 116. Because of this, the scintillation crystals 112 are used to absorb the high energy photons after the high energy photons have passed a significant distance into the scintillation crystals 112, and convert the high energy photons into a larger number of lower energy photons, which may be detected by the photodetectors 116. The larger number of lower energy photons are detected by the photodetector 116, creating a current pulse with a fast rising etch and a slow falling edge.

The output from the photodetectors 116 is provided to a channel 204, such as channel P shown in FIG. 3. In channel P, the output of the photodetector 116 is provided as input to the differential TIA 308, which converts an input current signal to an output voltage signal. The differential inputs from the photodetector 116 to the differential TIA 308 provide noise canceling. Differential output voltage signals from the differential TIA 308 are provided as input to the differential PGA 320. The differential PGA 320 amplifies the output of the differential TIA 308 and provides additional noise canceling. The output of the differential PGA 320 is provided as differential inputs to the differential comparators 328, 332, 336, which provide further noise canceling. The differential comparators 328, 332, 336 compare the differential inputs to the thresholds set by the DAC 504. In this example, if the input voltage is higher than the threshold voltage an output signal is generated by the differential comparators 328, 332, 336.

Output from the differential comparators 328, 332, 336 is recorded and time stamped by the first flip flop circuit 340 and the second flip flop circuit 344. The data from the flip flop circuit 340, which indicates voltage amplitude and time, is sent to the priority encoder 208, which sends the data to the FIFO buffer 212. The data in the FIFO buffer 212 is sent to the computer system 600 which matches the timing pulses with pulses detected by other scintillation crystals 112 to pair pulses as belonging to high energy photons created by the same annihilation event. The computer system 600 then uses the data to determine the location of the annihilation event. After collecting a large number of data, the computer system 600 is able to create an image.

Figure 7:
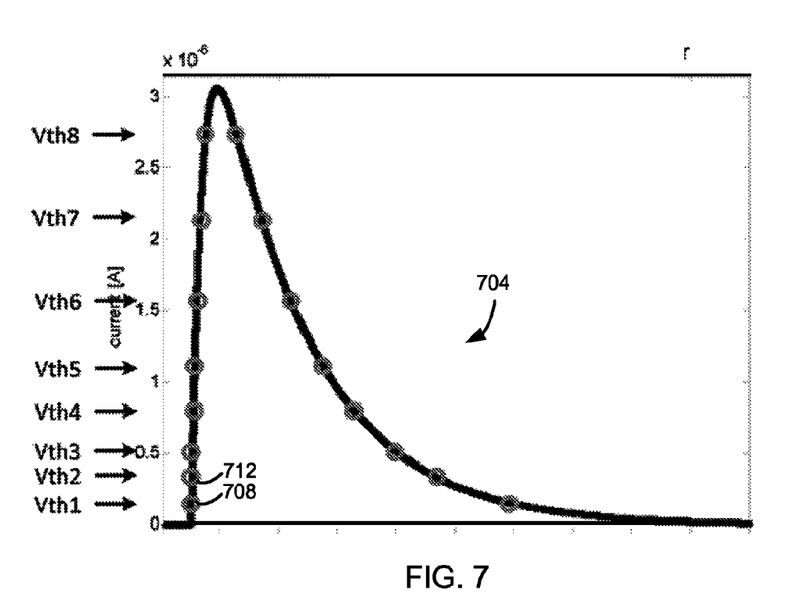
FIG. 7 is a graph of a readout of a PET signal pulse shape according to an embodiment.

FIG. 7 is a graph of a readout of a PET signal pulse shape 704 according to an embodiment. In this example, eight different threshold voltages are used. A first data point 708 is provided when the differential comparators record that the PET signal pulse shape 704 reaches a first threshold voltage by capturing the counter value. A second data point 712 is provided when the differential comparators record that the PET signal pulse shape 704 reaches a second threshold voltage by capturing the counter value. In this example, sixteen data points were obtained. Eight data points were obtained as the PET signal pulse shape 704 voltage increased passing each of the eight voltage thresholds, and eight data points were obtained as the PET signal pulse shape 704 voltage decreased passing each of the eight voltage thresholds.

This embodiment is able to accurately measure the fast rise leading edge of the PET signal pulse shape 704, which allows for an accurate time measurement and is able to accurately measure the trailing edge to accurately measure the energy information.

The differential TIA 308 allows for the embodiment to be adjustable for using different types of photodetectors, such as position sensitive avalanche photodiodes (PSAPD), silicon photomultipliers (SiPM), and photomultiplier tubes. In other embodiments, one type of photodetector may be selected and the embodiment may be designed for that photodetector, so that it is not necessary for the embodiment to be adjustable. In such a case, the switches and the option of two load resistors, $R_{large}$ and $R_{small}$, in the differential TIA 308 are not needed. The load resistor can be fixed to one value. Also, the differential programmable gain amplifier (PGA) 320 is not needed, or it can be replaced with an amplifier with a fixed gain and is not programmable. If the differential PGA is not needed, instead of the output of the differential TIA 308 being electrically connected to the inputs of the level-crossing ADC 324 through the differential PGA 320 in the above embodiment, the output of the differential TIA 308 may be electrically connected directly to the inputs of the level-crossing ADC 324, without passing through a differential PGA 320.

Figure 8:
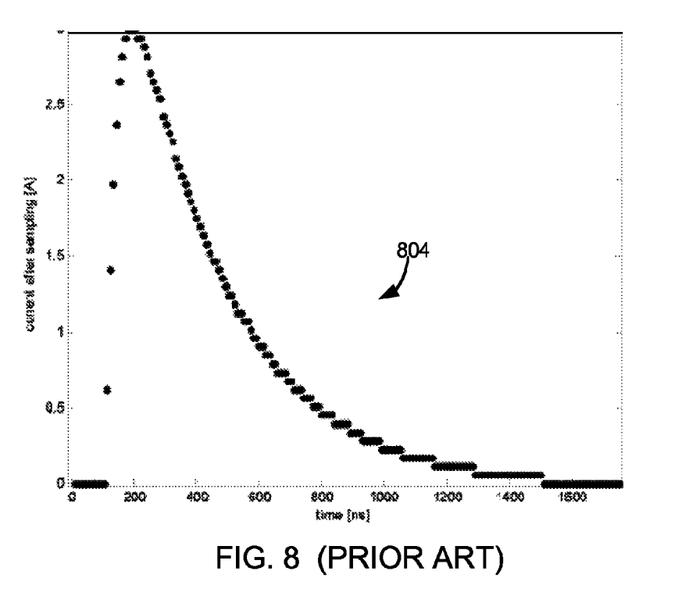
FIG. 8 is a graph of output from a conventional ADC recording a PET signal pulse shape.

A conventional readout device would use a conventional analog-to digital converter (ADC), which at set time intervals samples the pulse. FIG. 8 is a graph of output from a conventional ADC recording a PET signal pulse shape 804. Such a pulse has a fast rise and a slow fall. The sampling at set time intervals is an inefficient way to digitalize such pulses, when the goal is to have an excellent timing resolution of 100 to 300 pico seconds with a good energy resolution of 8%-15%. This goal is limited by the detector, because such sampling results in very few samples taken during the fast rising edge of the pulse, which results in degraded time resolution, and many samples on the slow falling edge of the pulse, where it is not necessary to have so many samples, since quantization noise is rejected when the pulse is integrated to obtain the energy of the pulse. Therefore, decreasing the time sampling interval to increase the sampling rate and the timing accuracy causes an increase in sampling of the slow falling edge, resulting in an increase in unneeded data. In addition, increasing the sampling rate is more expensive and power consuming.

While this invention has been described in terms of several preferred embodiments, there are alterations, permutations, modifications and various substitute equivalents, which fall within the scope of this invention. It should also be noted that there are many alternative ways of implementing the methods and apparatuses of the present invention. It is therefore intended that the following appended claims be interpreted as including all such alterations, permutations, modifications, and various substitute equivalents as fall within the true spirit and scope of the present invention.

The invention claimed is:

1. An integrated circuit in a PET imaging system with a plurality of photodetectors, wherein the plurality of photodetectors are optically coupled to scintillation crystals for a PET scanner, comprising:
    a plurality of differential transimpedance amplifiers with differential inputs and differential outputs, wherein differential inputs for each differential transimpedance amplifier of the plurality of differential transimpedance amplifiers are electrically connected to a photodetector of the plurality of photodetectors;
    a plurality of level crossing analog-to-digital converters wherein differential inputs for each level crossing analog-to-digital converter of the plurality of level crossing analog-to-digital converters are electrically connected to differential outputs of a differential transimpedance amplifier of the plurality of differential transimpedance amplifiers, wherein each level crossing analog-to-digital converter of the plurality of level crossing analog-to-digital converters, comprises:
        a plurality of differential comparators with differential inputs and differential threshold inputs, wherein the differential inputs are electrically connected to the output of the differential outputs of the differential transimpedance amplifier of the plurality of differential transimpedance amplifiers electrically connected to the level crossing analog-to-digital converter; and
        a clock for providing a time stamp, wherein each level crossing analog-to-digital converter of the plurality of level crossing analog-to-digital converters, further comprises a plurality of flip flops, wherein each flip flop receives input from a differential comparator of the plurality of differential comparators and the clock, wherein clock output is provided to a D input of each flip flop and differential comparator output is provided as input to a clock terminal of each flip flop, wherein output of each flip flop provides a digital representation of a shape of a current pulse waveform from a photodetector of the plurality of photodetectors.

2. The integrated circuit, as recited in claim 1, wherein each level crossing analog-to-digital converter of the plurality of level crossing analog-to-digital converters, further comprises
    a digital-to-analog converter comprising a plurality of resistors in series;
    a first n-to-1 multiplexer comprising a plurality of switches, which receives as input, output from between resistors of the plurality of resistors in series and provides output to first nodes of the differential threshold inputs of the plurality of differential comparators; and
    a second o-to-1 multiplexer comprising a plurality of switches, which receives as input, output from between resistors of the plurality of resistors in series and provides output to second nodes of the differential threshold inputs of the plurality of differential comparators.

3. The integrated circuit, as recited in claim 2, wherein the inputs to the o-to-1 multiplexer has a difference between adjacent levels which is at most equal to the voltage difference between the highest and lowest levels of the n-to-1 multiplexer plus the voltage difference between two consecutive levels of the n-to-1 multiplexer.

4. The integrated circuit, as recited in claim 3, wherein the clock, comprises:
    a phase locked loop;
    a Gray counter; and
    an interpolator.

5. The integrated circuit, as recited in claim 4, wherein the plurality of photodetectors are optically coupled to scintillation crystals for a PET scanner.

6. The integrated circuit, as recited in claim 5, further comprising a plurality of differential programmable gain amplifiers, wherein each differential programmable gain amplifier is electrically connected between the differential output of a differential transimpedance amplifier of the plurality of transimpedance amplifiers and the differential inputs of the plurality of differential comparators.

7. The integrated circuit, as recited in claim 1, wherein each differential transimpedance amplifier of the plurality of differential transimpedance amplifiers has at least two branches for high/low amplification and high/low impedance.

8. The integrated circuit, as recited in claim 1, wherein each level crossing analog-to-digital converter of the plurality of level crossing analog-to-digital converters, further comprises
    a digital-to-analog converter comprising a plurality of resistors in series;
    a first n-to-1 multiplexer comprising a plurality of switches, which receives as input, output from between resistors of the plurality of resistors in series and provides output to first nodes of the differential threshold inputs of the plurality of differential comparators; and
    a second o-to-1 multiplexer comprising a plurality of switches, which receives as input, output from between resistors of the plurality of resistors in series and provides output to second nodes of the differential threshold inputs of the plurality of differential comparators.

9. The integrated circuit, as recited in claim 8, wherein the inputs to the o-to-1 multiplexer has a difference between adjacent levels which is at most equal to the voltage difference between the highest and lowest levels of the n-to-1 multiplexer plus the voltage difference between two consecutive levels of the n-to-1 multiplexer.

10. The integrated circuit, as recited in claim 1, wherein the clock, comprises:
    a phase locked loop;
    a Gray counter; and
    an interpolator.

11. The integrated circuit, as recited in claim 1, further comprising a plurality of differential programmable gain amplifiers, wherein each differential programmable gain amplifier is electrically connected between the differential output of a differential transimpedance amplifier of the plurality of transimpedance amplifiers and the differential inputs of the plurality of differential comparators.

12. A PET imaging system, comprising:
    a plurality of scintillation crystals;
    a plurality of photodetectors, wherein each photodetector of the plurality of photodetectors is positioned to receive photons from a scintillation crystal of the plurality of scintillation crystals;
    an integrated circuit, comprising:
        a plurality of differential transimpedance amplifiers with differential inputs and differential outputs, wherein differential inputs for each differential transimpedance amplifier of the plurality of differential transimpedance amplifiers are electrically connected to a photodetector of the plurality of photodetectors;

a plurality of level crossing analog-to-digital converters wherein differential inputs for each level crossing analog-to-digital converter of the plurality of level crossing analog-to-digital converters are electrically connected to differential outputs of a differential transimpedance amplifier of the plurality of differential transimpedance amplifiers, wherein each level crossing analog-to-digital converter of the plurality of level crossing analog-to-digital converters, comprises:

a plurality of differential comparators with differential inputs and differential threshold inputs, wherein the differential inputs are electrically connected to the output of the differential outputs of the differential transimpedance amplifier of the plurality of differential transimpedance amplifiers electrically connected to the level crossing analog-to-digital converter;

a clock for providing a time stamp, wherein each level crossing analog-to-digital converter of the plurality of level crossing analog-to-digital converters, further comprises a plurality of flip flops, wherein each flip flop receives input from a differential comparator of the plurality of differential comparators and the clock, wherein clock output is provided to a D input of each flip flop and differential comparator output is provided as input to a clock terminal of each flip flop, wherein output of each flip flop provides a digital representation of a shape of a current pulse waveform from a photodetector of the plurality of photodetectors.

13. The PET imaging system, as recited in claim 12, wherein each level crossing analog-to-digital converter of the plurality of level crossing analog-to-digital converters, further comprises     a digital-to-analog converter comprising a plurality of resistors in series;

a first n-to-1 multiplexer comprising a plurality of switches, which receives as input, output from between resistors of the plurality of resistors in series and provides output to first nodes of the differential threshold inputs of the plurality of differential comparators; and     a second o-to-1 multiplexer comprising a plurality of switches, which receives as input, output from between resistors of the plurality of resistors in series and provides output to second nodes of the differential threshold inputs of the plurality of differential comparators.

14. The PET imaging system, as recited in claim 13, wherein the inputs to the o-to-1 multiplexer has a difference between adjacent levels which is at most equal to the voltage difference between the highest and lowest levels of the n-to-1 multiplexer plus the voltage difference between two consecutive levels of the n-to-1 multiplexer.

15. The PET imaging system, as recited in claim 14, wherein the clock, comprises:

a phase locked loop;

a Gray counter; and an interpolator.

16. The PET imaging system, as recited in claim 15, further comprising a plurality of differential programmable gain amplifiers, wherein each differential programmable gain amplifier is electrically connected between the differential output of a differential transimpedance amplifier of the plurality of transimpedance amplifiers and the differential inputs of the plurality of differential comparators.

\* \* \* \* \*